US00PP30139P2

(12) United States Plant Patent
Meilland

(10) Patent No.: US PP30,139 P2
(45) Date of Patent: Jan. 29, 2019

(54) BEDDING ROSE PLANT NAMED 'MEIMAULEVA'

(50) Latin Name: *Rosa hybrida*
Varietal Denomination: Meimauleva

(71) Applicant: The Conard-Pyle Company, West Grove, PA (US)

(72) Inventor: Alain Antoine Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 15/731,822

(22) Filed: Aug. 9, 2017

(51) Int. Cl.
*A01H 5/02* (2018.01)

(52) U.S. Cl.
USPC ..... Plt./102
CPC ..... *A01H 5/02* (2013.01)

(58) Field of Classification Search
USPC ..... Plt./102, 109
CPC ..... A01H 5/0222
See application file for complete search history.

(56) References Cited

U.S. PATENT DOCUMENTS

PP17,518 P3 3/2007 Cowlishaw

OTHER PUBLICATIONS https://issuu.com/starrosesandplants/docs/2018_catalog; Apr. 27, 2017; 1 page.*

* cited by examiner

*Primary Examiner* — Kent L Bell
(74) *Attorney, Agent, or Firm* — Buchanan Ingersoll & Rooney PC

(57) ABSTRACT

A new and distinct variety of Bedding rose plant, herein referred to by its cultivar name, 'Meimauleva', is provided which forms in abundance on a substantially continuous basis attractive, flat cup-shaped, red-purple colored blossoms. Attractive, semi-glossy foliage is formed and the plant is very floriferous. The tolerance to disease is good, particularly with respect to black spot. The new variety is well suited for providing attractive ornamentation in the landscape.

1 Drawing Sheet

Figures 1, 2, 3, 4, 5, 6, 7, 8, 9, 10, 11, 12, 13, 14, 15:
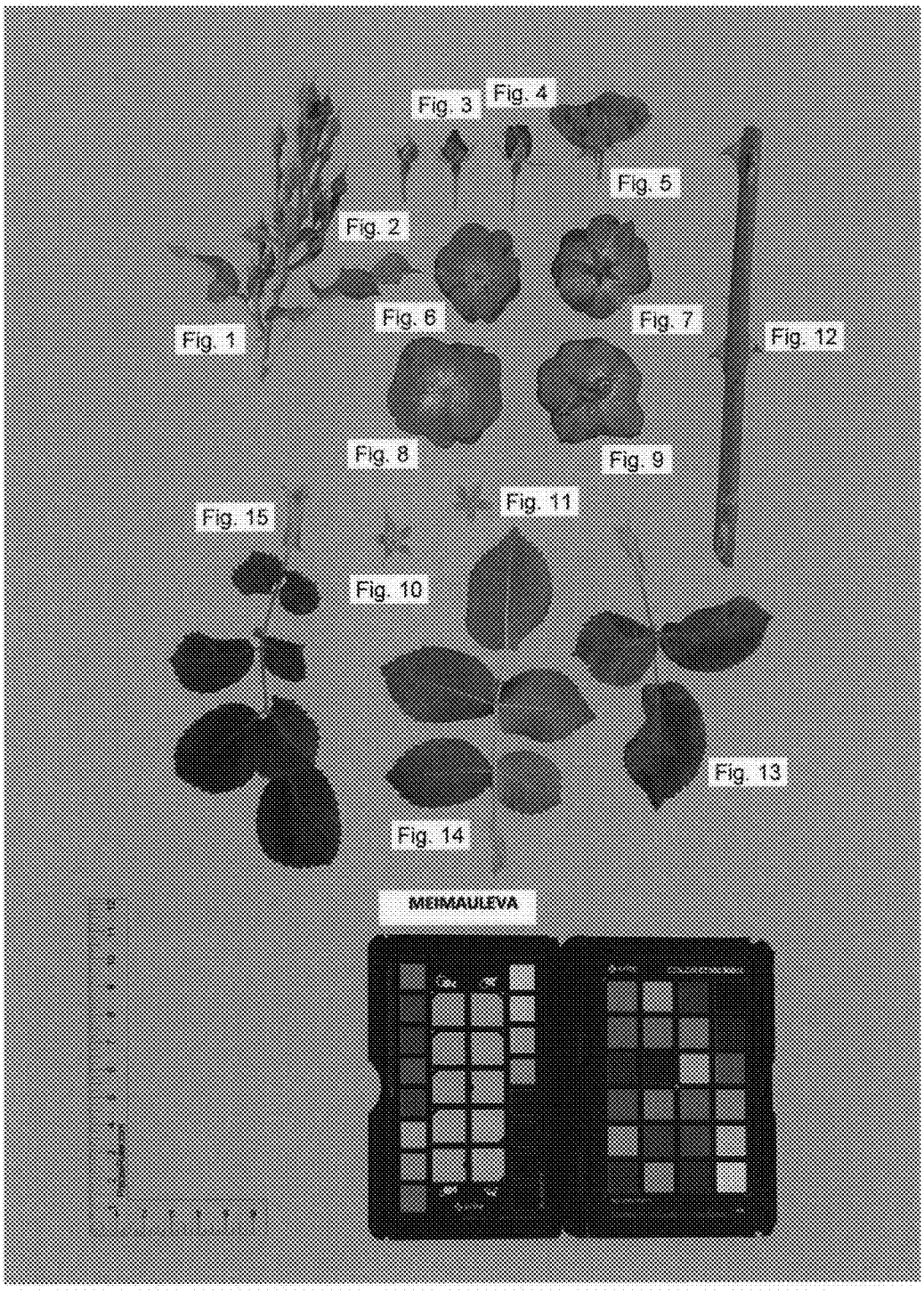

Botanical/commercial classification:
Latin name—*Rosa hybrida.*
Common name—Bedding Rose Plant.
Varietal denomination—'Meimauleva'.

SUMMARY OF THE INVENTION

The new variety of *Rosa hybrida* Bedding rose plant of the present invention was created by artificial pollination wherein two parents were crossed which previously had been studied in the hope that they would contribute the desired characteristics. The female parent (i.e., seed parent) of the new variety was the 'The Fairy' variety (non-patented). The male parent (i.e., pollen parent) was the 'Frantasia' variety (U.S. Plant Pat. No. 17,518).

The parentage can be summarized as follows:

'The Fairy' x 'Frantasia'.

The seeds resulting from the above pollination were sown and small plants were obtained which were physically and biologically different from each other. Selective study resulted in the identification of a single plant of the new variety.

It was found that the new Bedding rose plant of the present invention possesses the following combination of characteristics:

(a) displays a vigorous plant,
(b) shows a red-purple coloration of the flower which is a beautiful contrast with the semi-glossy foliage, (c) is very floriferous,
(d) exhibits good tolerance to disease, particularly with respect to black spot, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, blooms of the 'The Fairy' variety display clear pink coloration, while the new variety displays red-purple coloration of the blooms. Further, while the new variety commonly displays 8 petals per bloom on average, the 'Frantasia' variety has between 13 to 17 petals per bloom on average.

The new variety has been found to undergo asexual propagation in France by a number of routes, including budding, grafting, and the rooting of cuttings. Asexual propagation by the above-mentioned techniques in France has shown that the characteristics of the new variety are stable and strictly transmissible by such asexual propagation from one generation to another. Accordingly, the new variety undergoes asexual propagation in a true-to-type manner.

The new variety has been named 'Meimauleva'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately one year of age and were observed during June while budded on their own roots and growing outdoors at Le Cannet des Maures, Var, France. Dimensions in centimeters are indicated at the bottom of the photograph. Standard color information is included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening to the petals.

FIG. 5—illustrates a specimen of a flower in the course of opening.

FIG. 6—illustrates a specimen of a flower in the course of opening—plan view—obverse.

FIG. 7—illustrates a specimen of a flower in the course of opening—plan view—reverse.

FIG. 8—illustrates a specimen of a fully open flower—plan view—obverse.

FIG. 9—illustrates a specimen of a fully open flower—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 3 leaflets—plan view—upper surface.

FIG. 14—illustrates a specimen of a leaf with 5 leaflets—plan view—under surface.

FIG. 15—illustrates a specimen of a leaf with 7 leaflets—plan view—upper surface.

DETAILED BOTANICAL DESCRIPTION

The chart used in the identification of colors is that of The Royal Horticultural Society (R.H.S. Colour Chart, 2001 edition), London, England. The terminology which precedes reference to the chart has been added to indicate the corresponding color in more common terms. The description is based on the observation of one-year-old specimens of the new variety during June while budded on their own roots and growing outdoors at Le Cannet des Maures, Var, France.

Class: Bedding Rose.

Plant:

*Habit*.—Bushy.

Branches:

*Color*.—Commonly near Yellow Green Group 144A on young stems, and commonly near Yellow Green Group 147B on adult wood.

*Thorns*.—Configuration on adult stems: elongated and curved downwards on the upper surface and concave on the under surface with an oval shape at the base. Long prickles (≥0.6 cm) — quantity: commonly approximately 8 thorns per 10 cm long young stem and commonly approximately 6 thorns per 10 cm long adult stems. Long prickles (≥0.6 cm) — color: commonly near Yellow Green Group 150B on young stems and commonly near Greyed Orange Group 164A on adult stems. Long prickles (≥0.6 cm) — size: commonly 0.7-0.8 cm in length on average on young stems and commonly near 0.6 cm in length on average on adult stems. Small prickles (<0.6 cm) — quantity: commonly approximately 62 thorns per 10 cm long young stem and commonly approximately 6 thorns per 10 cm long adult stem. Small prickles (<0.6 cm) — color: commonly near Yellow Green Group 150B on young stems and commonly near Greyed Orange Group 164A on adult stems. Small prickles (<0.6 cm) — size: commonly 0.1-0.2 cm on average in length on young stems and approximately 0.1 cm on average in length on adult stems.

Foliage:

*General appearance*.—Rather dense with a semi-glossy aspect.

*Leaf*.—Length: approximately 10.5 cm to 13 cm on average. Width: approximately 6.5 cm to 7.5 cm on average.

*Number of leaflets*.—3, 5, and 7; most often 5 or 7.

*Terminal leaflet*.—Length: approximately 3.5 cm on average. Width: approximately 2.9 cm on average.

*New foliage*.—Upper surface color: commonly near Green Group 137C. Under surface color: commonly near Yellow Green Group 148B.

*Adult foliage*.—Upper surface color: commonly near Yellow Green Group 147A. Under surface color: commonly near Yellow Green Group 146C.

Leaflets:

*Shape*.—Tip: cupsidate. Base: obtuse.

*Texture*.—Leathery.

*General appearance*.—Oval.

*Edge*.—Slightly denticulate.

*Serration*.—Small and single.

*Rachis*.—Color of upper surface: commonly near Yellow Green Group 148C. Color of under surface: commonly near Yellow Green Group 147D.

*Petioles*.—Upper surface texture: glandular, with a few glands and small hairs. Under surface texture: few prickles. Color of upper surface: commonly near Yellow Green Group 146B. Color of under surface: commonly near Yellow Green Group 147D. Petiole length of terminal leaflet: near 3.4 cm on average.

*Stipules*.—General appearance: adnate, pectinate and rather broad. Length: near 1.4 cm on average. Width: near 0.6 cm on average. Color of upper surface: commonly near Yellow Green Group 146B. Color of under surface: commonly near Yellow Green Group 147D.

Inflorescence:

*Number of flowers per stem*.—Commonly singly or in a cluster of approximately 2 to 4 blossoms per stem on average.

*Buds*.—Shape: conical. Size: small. Length: approximately 0.9 cm on average. Width: approximately 0.6 cm on average. Color as calyx breaks — upper surface: commonly near Red Purple Group 73C to Red Purple 74B. Color as calyx breaks — under surface: commonly near Red Purple Group 74D to Red Purple group 74A.

*Sepals*.—Length: approximately 1.5 cm on average. Width: near 0.5 cm on average. Shape: without extension; base is upright; top is longish. Upper surface — texture: tomentous. Upper surface — color: commonly near Green Group 138C. Under surface — texture: smooth. Under surface — color: commonly near Green Group 139C.

*Receptacle*.—Color: commonly near Green Group 139C. Length: approximately 1.1 cm on average. Width: approximately 1 cm on average. Surface: smooth. Shape: funnel shaped.

*Peduncle*.—Length: near 3 to 5 cm on average. Width: approximately 0.3 cm on average. Surface: smooth. Color: commonly near Green Group 139C.

*Flower*.—Average open size: near 5 cm. Shape: flat cup shaped. Number of petals: commonly 8 petals. Shape of petal: Base: obtuse. Top: rounded. Texture of the petal: leathery. Petal length: approximately 2 cm on average. Petal width: Approximately 2 cm on average. Petal arrangement: imbricated without petaloids. Petal drop: petals drop off cleanly before drying. Fragrance: none. Color when opening — upper surface: commonly near Red Purple Group 73C amply bordered with near Red Purple Group 74B. Color when opening — under surface: commonly near Red Purple Group 74D bordered with near Red Purple Group 74A. Color of the open flower — upper surface: commonly near Purple Group 75C bordered and suffused with near Red Purple Group 74B. Color of the open flower — under surface: commonly near Purple Group 75C bordered and suffused with near Red Purple Group 74B. Anthers: number is approximately 57 on average, length is approximately 0.1 cm on average, coloration is commonly between Yellow Orange Group 17B and Yellow Orange Group 17C, and arrangement is regular around styles. Filaments: length is approximately 0.2 cm on average, and coloration is near Yellow Orange Group 16D. Styles: number is approximately 17 on average, length is approximately 0.1 cm on average, and coloration is commonly near Orange Group 24D. Stigmas: size is approximately 0.2 cm on average and coloration is commonly near Yellow Group 2D. Hip: rounded shape and near 1 cm in size on average.

Development:

*Vegetation*.—Strong.

*Blooming*.—Early in the season, very abundant and nearly continuous.

*Tolerance to diseases*.—Good, and particularly against black spot (*Diplocarpon rosae*).

Plants of the 'Meimauleva' variety have not been observed under all possible environmental conditions to date. Accordingly, it is possible that the phenotypic expression may vary somewhat with changes in light intensity and duration, cultural practices, and other environmental conditions.

I claim:

1. A new and distinct Bedding rose plant characterized by the following combination of characteristics:

(a) displays a vigorous plant, (b) shows a red purple coloration of the flower which is a beautiful contrast with the semi-glossy foliage, (c) is very floriferous, (d) exhibits good tolerance to disease, particularly with respect to black spot, and (e) is well suited for providing attractive ornamentation; substantially as herein shown and described.

* * * * *

MEIMAULEVA